United States Patent [19]
Gendrot et al.

[11] Patent Number: 6,039,979
[45] Date of Patent: Mar. 21, 2000

[54] MULTIPARTICULATE PHARMACEUTICAL FORM WITH PROGRAMMED AND PULSED RELEASE AND PROCESS FOR ITS PREPARATION

[75] Inventors: Edouard Gendrot, Garnay; Gérard Cousin, Le Mesnil Ponceau; Françoise Ragot, Leves; Marie-Christine Clee-Bouvet, Treon, all of France

[73] Assignee: Laboratoires Prographarm, France

[21] Appl. No.: 09/229,864

[22] Filed: Jan. 13, 1999

[51] Int. Cl.⁷ ........................................ A61K 9/14
[52] U.S. Cl. ........................ 424/497; 424/494; 424/456
[58] Field of Search .................... 424/489, 465, 424/464, 479, 493, 495, 480, 456

[56] References Cited

U.S. PATENT DOCUMENTS

| | | | |
|---|---|---|---|
| 5,508,044 | 4/1996 | Buxton et al. | 424/495 |
| 5,567,441 | 10/1996 | Chen . | |
| 5,705,092 | 1/1998 | Wellinghoff et al. | 252/187.21 |

FOREIGN PATENT DOCUMENTS

| | | |
|---|---|---|
| 0 463 877 | 1/1992 | European Pat. Off. . |
| WO 98/17261 | 4/1998 | WIPO . |

OTHER PUBLICATIONS

"An organic Acid-Induced Sigmoidal Release System for Oral Controlled-Release Preparations", Pharmaceutical Research, vol. 11, No. 1 (1994), pp. 111–116.

*Primary Examiner*—Thurman K. Page
*Assistant Examiner*—W. Benston
*Attorney, Agent, or Firm*—Caesar, Rivise, Bernstein, Cohen & Pokotilow, Ltd.

[57] ABSTRACT

The invention relates to a multiparticulate pharmaceutical form with delayed and pulsed release, enabling to obtain the onset of the availability of the active ingredient within 4 to 8 hours after the ingestion of the pharmaceutical form, and then a progressive release of the totality of the active ingredient within the 8 to 20 following hours, characterized by the fact that it is free of organic acid and that it is in the form of medicinal spheroids consisting of a neutral spherical core comprising a first coating based on a mixture of at least one hydrosoluble polymer and of at least one non hydrosoluble polymer throughout which are uniformly distributed the constitutive particles of an active ingredient, the whole comprising a second coating based on at least two pH independent polymers presenting rates of permeability different from one another with respect to the gastric and intestinal mediums, optionally at least one pH dependent polymer, at least one plasticizer and at least one inert carrier uniformly distributed throughout the said coating.

15 Claims, No Drawings

MULTIPARTICULATE PHARMACEUTICAL FORM WITH PROGRAMMED AND PULSED RELEASE AND PROCESS FOR ITS PREPARATION

The invention relates to a multiparticulate pharmaceutical form, with programmed and pulsed release, intended for oral administration. It also relates to the process for the preparation of the said pharmaceutical form.

Numerous pharmaceutical forms with delayed release for oral administration are available. The release of the active ingredient must be controlled as a function of the therapeutical purpose and of the pharmacological properties of the active ingredient. In consequence, it is not always desirable that the plasmatic rate be constant. On the contrary, in order to avoid any habituation and in order to limit the side effects provoked by the active ingredient, it would be absolutely advantageous for the plasmatic rate to follow the metabolic rhythm and the specific needs of the patient during certain periods of the nycthemer. For instance, in order to diminish the nocturnal symptoms or the symptoms upon awakening in the case of certain chronic diseases such as ischemic heart disease, asthma and arthritis, the drugs should be administered such a way that the desired therapeutical plasmatic level is reached only at the desired moment, that is to say during sleep or just at the moment of awakening.

In the article "An Organic Acid-Induced Sigmoidal Release System for Oral Controlled-Release Preparations", Pharmaceutical Research, Vol. 11, No. 1 (1994), is disclosed a pharmaceutical form wherein the release of the active ingredient is of the sigmoidal type. However, it is indicated in this article that the sigmoidal release of the active ingredient can be obtained only if an organic acid is added to the pharmaceutical form. However, due to the presence of an organic acid, such pharmaceutical forms may have an irritating effect, which constitutes a major drawback especially in the case of long lasting treatments.

Consequently, there does not exist at present a multiparticulate pharmaceutical form free of organic acid, capable of making available high concentrations of active ingredient at the moment at which the patient needs them the most, while maintaining the minimal therapeutical plasmatic concentration throughout the day.

The Applicants have had the merit of finding unexpectedly and surprisingly that it is possible to obtain such pharmaceutical forms which are easy for administration and which do not present an irritating effect.

Thus, the multiparticulate pharmaceutical form according to the invention wherein the release of the active ingredient is delayed and pulsed and which enables to obtain the onset of the availability of the active ingredient within 4 to 8 hours after the ingestion of the pharmaceutical form, and then a progressive release of the totality of the active ingredient within the 8 to 20 following hours, is characterized by the fact that it is free of organic acid and that it is in the form of microgranules or medicinal spheroids consisting of a neutral spherical core comprising a first coating based on a mixture of at least one hydrosoluble polymer and of at least one non hydrosoluble polymer throughout which are uniformly distributed the constitutive particles of an active ingredient, the whole comprising a second coating based on at least two pH independent polymers presenting rates of permeability different from one another with respect to the gastric and intestinal mediums, optionally at least one pH dependent polymer, at least one plasticizer and at least one inert carrier uniformly distributed throughout the said coating.

The concentration of active ingredient is very high in the coating which envelops the neutral spherical core which makes it possible to obtain medicinal spheroids of reduced size and thus definite pharmaceutical forms of low size which are easier and more pleasant to be ingested by the patient and which permit the administration of higher dosages per administered drug unit.

According to an advantageous embodiment, the pharmaceutical form according to the invention is thus characterized by the fact that the active ingredient represents from 20 to 100% by weight of the coating which envelops a neutral spherical core, preferably from 60 to 90% by weight and still more preferably from 80 to 90% by weight.

The hydrosoluble polymer which is part of the composition of the coating which envelops the neutral spherical core and which contains the active ingredient is selected from the group comprising especially polyvinylpyrrolidone, hydroxypropylmethyl cellulose, and their mixtures, and the non hydrosoluble polymer is selected from the group comprising especially acrylic and/or methacrylic resins, cellulosic polymers, and their mixtures.

The weight ratio between the hydrosoluble polymer and the non hydrosoluble polymer is from 0.1 to 0.9, preferably from 0.3 to 0.7, and still more preferably from 0.45 to 0.55.

The second coating of the pharmaceutical form according to the invention is based on at least two pH independent polymers which present permeability rates which are different from one another with respect to the gastric and the intestinal mediums, optionally at least one pH dependent polymer, at least one plasticizer and at least one inert carrier uniformly distributed throughout the said coating.

In this second coating, the proportion between the polymer which presents the lowest permeability and the polymer which presents the highest permeability, is from 97/3 to 80/20.

It is necessary to respect these proportions between the polymers of different permeability rates. As a matter of fact, in the case of proportions of polymer of low permeability higher than 97%, the release of the active ingredient can be too much delayed; on the contrary, in the case of proportions of polymer of low permeability lower than 80%, the release of the active ingredient is not sufficiently delayed.

The polymers of the second coating are selected from the group comprising especially acrylic and/or methacrylic resins, cellulosic polymers, and their mixtures.

The inert carrier which is uniformly distributed throughout the second coating is selected from the group comprising especially talc, anhydrous colloidal silicone dioxide, magnesium stearate, monostearate of glycerol and their mixtures.

The plasticizer which is part of the constitution of the second coating must be pharmaceutically acceptable; it is selected from the group comprising especially ethylphthalate, triethylcitrate, dibutylsebacate, triacetine and their mixtures.

According to an advantageous embodiment of the invention, the active ingredient is selected from the group comprising especially the molecules which are active on the cardio-vascular system, and more especially Diltiazem and Verapamil, the anti-inflammatories, the antiallergics and the antihistamines.

The pharmaceutical form according to the invention is administered at bed-time.

Thus, the availability of the active ingredient begins about 4 to 8 hours after ingestion, that is to say at the moment of awakening of the patient, i.e. the moment at which certain of the symptoms among which the risks of cardio-vascular accidents are the highest.

The release continues regularly throughout the following 8 to 20 hours.

The administration of the next pharmaceutical form being carried out several hours after the end of the total release of the active ingredient, the patient has the benefit of the minimal therapeutical plasmatic concentration during the whole nycthemer.

The process according to the invention for the preparation of the pharmaceutical form according to the invention is characterized by a sequence of steps comprising:

the introduction of neutral spherical cores into a reaction vessel working on the principle of the fluidised-bed, the spraying onto the said neutral spherical cores of particles of the active ingredient suspended in a solution of at least one hydrosoluble polymer and of at least one non hydrosoluble polymer in an organic and/or aqueous solvent, the spraying on the coated particles obtained in the preceding step of a coating suspension comprising at least one inert carrier suspended in a solution of a mixture of at least two polymers having permeabilities different from one another with respect to the gastric and the intestinal mediums, optionally the drying of the medicinal spheroids thus obtained.

EXAMPLES

In the following examples, the following pharmaceutical excipients are used:

EUDRAGIT RS 100: polyacrylic-polymethacrylic resin of low permeability marketed by RÖHM, EUDRAGIT RL 100: permeable polyacrylate-polymethacrylate resin marketed by RÖHM, PVP K 90: polyvinylpyrrolidone marketed by BASF, AEROSIL: silica gel marketed by DEGUSSA, Alcohol for pharmaceutical use, Talc for pharmaceutical use, Ethyl phthalate marketed by SOLVAY, Spherical neutral cores consisting of saccharose and of starch marketed by the Company WERNER's, INWITOR 900: glycerol monostearate marketed by the Company UHLS, EUDRAGIT L 100: resin based on methacrylic acid and on methyl methacrylate marketed by RÖHM.

EXAMPLE 1

Preparation of medicinal spheroids constituted of the pharmaceutical form according to the invention and whose active ingredient is Diltiazem.

0.7 kg of neutral spherical cores having a diameter from 300 to 400 μm are introduced in a fluidized air bed reaction vessel of the GPCG1 type and on the said cores there is sprayed a suspension having the following composition:

| EUDRAGIT RS 100 | 0.525 kg |
| PVP K 90 | 0.525 kg |
| Diltiazem | 7.000 kg |
| Alcohol for pharmaceutical use | 18.760 kg. |

Then, a coating suspension is sprayed on the thus obtained particles, which suspension has the following composition:

| EUDRAGIT RS 100 | 2.000 kg |
| EUDRAGIT RL 100 | 0.100 kg |
| Ethyl phthalate | 0.192 kg |
| AEROSIL | 0.320 kg |
| Talc for pharmaceutical use | 0.400 kg |
| Alcohol for pharmaceutical use | 10.500 kg |
| Acetone | 4.500 kg. |

400 to 500 of the thus obtained medicinal spheroids are introduced in hard capsules of gelatin having a classical constitution.

A release test in vitro of the active ingredient is carried out as follows:

A conventional dissolumeter equipped with pales is used; purified water is used as dissolution medium; the use conditions of the dissolumeter are 900 ml of purified water and 100 rpm; the amount of introduced capsules corresponds to one therapeutical unit.

The amount of active ingredient released (expressed in percent by weight) with respect to the total amount of active ingredient comprised in the introduced capsules is measured as follows:

Sampling of the solution is carried out, every hour, from time 0 to 4 hours and then, every two hours, from the 4th to the 16th hour. The released Diltiazem in the sample solutions is determined by way of an HPLC device equipped with an UV detector at 240 nm.

The results obtained are collected in Table 1.

TABLE 1

| HOURS | % DISSOLVED |
|---|---|
| 0 | 0 |
| 1 | 0.8 |
| 2 | 2.0 |
| 3 | 3.4 |
| 4 | 5.1 |
| 6 | 11.7 |
| 8 | 40.4 |
| 10 | 88.0 |
| 12 | 99.4 |
| 14 | 100.9 |

EXAMPLE 2

Preparation of medicinal spheroids constituted of the pharmaceutical form according to the invention and whose active ingredient is Diltiazem.

Medicinal spheroids are prepared as indicated in example 1 using as coating suspension a suspension having the following composition:

| EUDRAGIT RS 100 | 3.060 kg |
| EUDRAGIT RL 100 | 0.340 kg |
| Ethyl phthalate | 0.340 kg |
| Inwitor 900 | 0.170 kg |
| Isopropanol | 14.28 kg |
| Acetone | 9.52 kg. |

According to the same way as in example 1, the dissolution is measured. The results are collected in table 2 hereafter.

TABLE 2

| HOURS | % DISSOLVED |
|---|---|
| 0 | 0 |
| 1 | 2.8 |
| 2 | 6.4 |
| 3 | 11.6 |
| 4 | 18.4 |
| 6 | 32.3 |
| 8 | 49.1 |
| 10 | 68.7 |
| 12 | 85.3 |
| 16 | 103.6 |

EXAMPLE 3

Preparation of medicinal spheroids constituted of the pharmaceutical form according to the invention and whose active ingredient is Diltiazem.

Medicinal spheroids are prepared as indicated in example 1 using as coating suspension a suspension having the following composition:

| | |
|---|---|
| EUDRAGIT RS 100 | 3.612 kg |
| EUDRAGIT RL 100 | 0.638 kg |
| Ethyl phthalate | 0.425 kg |
| Inwitor 900 | 0.213 kg |
| Isopropanol | 17.850 kg |
| Acetone | 11.900 kg. |

According to the same way as in example 1, the dissolution is measured. The results are collected in table 3 hereafter.

TABLE 3

| HOURS | % DISSOLVED |
|---|---|
| 0 | 0 |
| 1 | 1.1 |
| 2 | 7.2 |
| 3 | 84.3 |
| 4 | 90 |
| 6 | 92.7 |
| 8 | 94.8 |
| 10 | 94 |
| 12 | 95.1 |
| 14 | 95.1 |
| 16 | 96 |

EXAMPLE 4

Preparation of medicinal spheroids constituted of the pharmaceutical form according to the invention and whose active ingredient is Verapamil.

Medicinal spheroids are prepared in the same way in example 1, Diltiazem being substituted as active ingredient by Verapamil, coating suspension consisting of a suspension having the following composition:

| | |
|---|---|
| EUDRAGIT RS 100 | 1.650 kg |
| EUDRAGIT RL 100 | 0.87 kg |
| EUDRAGIT L 100 | 0.063 kg |
| Ethyl phthalate | 0.165 kg |
| AEROSIL | 0.274 kg |
| Talc | 0.343 kg |
| Alcohol for pharmaceutical use | 9.000 kg |
| Acetone | 3.857 kg. |

According to the same way as in example 1, the dissolution is measured, the released Verapamil being determined by way of a spectrophotometer UV at 278 nm. The results are collected in table 4 hereafter.

TABLE 4

| HOURS | % DISSOLVED |
|---|---|
| 0 | 0 |
| 1 | 1.9 |
| 2 | 6.1 |
| 3 | 12.3 |
| 4 | 21.2 |
| 6 | 49.6 |
| 8 | 82.1 |
| 10 | 94.7 |
| 12 | 97.4 |
| 14 | 97.8 |
| 16 | 98.6 |

What is claimed is:

1. Multiparticulate pharmaceutical form with delayed and pulsed release of the active ingredient, enabling to obtain the onset of the availability of the active ingredient within 4 to 8 hours after the ingestion of the pharmaceutical form, and then to progressive release of the totality of the active ingredient within the 8 to 20 following hours, the said multiparticulate pharmaceutical form which is free of organic acid, comprising medicinal spheroids including each a neutral spherical core enveloped by a first coating based on a mixture of at least one hydrosoluble polymer and of at least one non hydrosoluble polymer throughout which are uniformly distributed the constitutive particles of an active ingredient, the cores coated with the first coating comprising a second coating based on at least two pH independent polymers presenting rates of permeability different from one another with respect to the gastric and intestinal mediums.

2. Pharmaceutical form according to claim 1, wherein the active ingredient represents from 20 to 100% by weight of the coating which envelops the neutral spherical core.

3. Pharmaceutical form according to claim 1, wherein the active ingredient represents from 60 to 90% by weight of the coating which envelops the neutral spherical core.

4. Pharmaceutical form according to claim 1, wherein the active ingredient represents from 80 to 90% by weight of the coating which envelops the neutral spherical core.

5. Pharmaceutical form according to claim 1, wherein the weight ratio between the hydrosoluble polymer and the non hydrosoluble polymer is from 0.1 to 0.9.

6. Pharmaceutical form according to claim 1, wherein the weight ratio between the hydrosoluble polymer and the non hydrosoluble polymer is from 0.3 to 0.7.

7. Pharmaceutical form according to claim 1, wherein the weight ratio between the hydrosoluble polymer and the non hydrosoluble polymer is 0.45 to 0.55.

8. Pharmaceutical form according to claim 1, wherein the hydrosoluble polymer is selected from the group comprising especially polyvinylpyrrolidone, hydroxy-propylmethyl cellulose and their mixtures, and the non hydrosoluble polymer is selected from the group comprising especially acrylic and/or methacrylic resins, cellulosic polymers and their mixtures.

9. Pharmaceutical form according to claim 1, wherein the proportion between the polymer which presents the lowest permeability and the polymer which presents the highest permeability, is from 97/3 to 80/20.

10. Pharmaceutical form according to claim 1, wherein the polymers of the second coating are selected from the group comprising especially acrylic and/or methacrylic resins, cellulosic polymers and their mixtures.

11. Pharmaceutical form according to claim 1, wherein the inert carrier which is uniformly distributed throughout the second coating is selected from the group comprising especially talc, anhydrous colloidal silicone dioxide, magnesium stearate, monostearate of glycerol and their mixtures.

12. Pharmaceutical form according to claim 1, wherein it is administered at bed-time.

13. Pharmaceutical form according to claim 1, wherein the active ingredient is selected from the group comprising especially the molecules which are active on the cardiovascular system, and more especially Diltiazem and Verapamil, the anti-inflammatories, the antiallergics and the antihistamines.

14. Process for the preparation of the pharmaceutical form according to claim 1, comprising:

the introduction of neutral spherical cores into a reaction vessel working on the principle of the fluidised-bed, the spraying onto the said neutral spherical cores of particles of the active ingredient suspended in a solution of at least one hydrosoluble polymer and of at least one non hydrosoluble polymer in an organic and/or aqueous solvent, the spraying on the coated particles obtained in the preceding step of a coating suspension comprising at least one inert carrier suspended in a solution of a mixture of at least two polymers having permeabilities different from one another with respect to the gastric and the intestinal mediums.

15. Multiparticulate pharmaceutical form according to claim 1 wherein the second coating comprises at least one pH dependent polymer, at least, one plasticizer and at least one inert carrier uniformly distributed throughout said coating.

* * * * *